(12) United States Patent
McLeod et al.

(10) Patent No.: US 9,867,636 B2
(45) Date of Patent: Jan. 16, 2018

(54) METHOD, APPARATUS, AND A SYSTEM FOR A WATER JET

(71) Applicant: The Regents of the University of California, Oakland, CA (US)

(72) Inventors: Stephen McLeod, San Francisco, CA (US); Reza Zadno, Menlo Park, CA (US)

(73) Assignee: The Regents of the University of California, Oakland, CA (US)

( * ) Notice: Subject to any disclaimer, the term of this patent is extended or adjusted under 35 U.S.C. 154(b) by 253 days.

(21) Appl. No.: 14/212,863

(22) Filed: Mar. 14, 2014

(65) Prior Publication Data
US 2014/0316392 A1     Oct. 23, 2014

Related U.S. Application Data

(60) Provisional application No. 61/793,108, filed on Mar. 15, 2013.

(51) Int. Cl.
*A61B 17/3203* (2006.01)
*A61F 9/008* (2006.01)
*A61F 9/007* (2006.01)
*A61B 90/00* (2016.01)

(52) U.S. Cl.
CPC ...... *A61B 17/3203* (2013.01); *A61F 9/00736* (2013.01); *A61F 9/00825* (2013.01); *A61B 2090/049* (2016.02); *A61F 2009/0087* (2013.01); *A61F 2009/00887* (2013.01)

(58) Field of Classification Search
CPC .......... A61B 17/3203; A61B 17/32037; A61B 2017/32032; A61B 2017/32035; A61F 9/00736; A61F 9/00709; A61F 9/0013; A61M 1/0084; A61M 25/007; B05B 1/14; B05B 1/20; B05B 1/205; B05B 1/207
See application file for complete search history.

(56) References Cited

U.S. PATENT DOCUMENTS

| | | | | |
|---|---|---|---|---|
| 3,818,913 A | * | 6/1974 | Wallach | A61F 9/00736 604/28 |
| 3,930,505 A | * | 1/1976 | Wallach | A61M 1/0084 604/22 |
| 4,735,620 A | * | 4/1988 | Ruiz | A61M 25/0041 604/264 |
| 5,135,482 A | * | 8/1992 | Neracher | A61B 17/32037 604/22 |
| 5,199,512 A | * | 4/1993 | Curlett | E21B 10/60 175/393 |
| 5,735,815 A | * | 4/1998 | Bair | A61B 17/3203 604/22 |
| 5,766,194 A | * | 6/1998 | Smith | A61B 17/3203 606/1 |
| 5,989,271 A | * | 11/1999 | Bonnette | A61B 17/32037 604/22 |
| 6,106,516 A | * | 8/2000 | Massengill | A61B 17/3203 606/15 |
| 6,135,977 A | * | 10/2000 | Drasler | A61B 17/32037 604/22 |

(Continued)

*Primary Examiner* — Dianne Dornbusch
(74) *Attorney, Agent, or Firm* — Edward J. Baba; Shweta Chandra; Bozicevic, Field & Francis LLP

(57) ABSTRACT

A fluid or laser jet instrument may be used for manually performing eye surgery or any emulsification technique.

12 Claims, 4 Drawing Sheets

(56) References Cited

U.S. PATENT DOCUMENTS

| | | | |
|---|---|---|---|
| 6,289,902 B1 * | 9/2001 | Mathiez | A46B 9/021 132/218 |
| 6,676,627 B1 * | 1/2004 | Bonnette | A61M 1/0084 604/22 |
| 6,676,637 B1 * | 1/2004 | Bonnette | A61B 17/32037 604/165.02 |
| 7,815,632 B2 * | 10/2010 | Hayakawa | A61B 17/32037 604/19 |
| 7,967,799 B2 | 6/2011 | Boukhny | |
| 8,574,226 B2 * | 11/2013 | Shadduck | A61B 18/04 606/27 |
| 9,061,299 B1 * | 6/2015 | Fodor | B05B 13/0436 |
| 9,078,691 B2 * | 7/2015 | Morris | A61B 17/32037 |
| 9,526,863 B2 * | 12/2016 | Baxter | A61B 17/22 |
| 2003/0009132 A1 * | 1/2003 | Schwartz | A61M 5/158 604/152 |
| 2003/0125660 A1 * | 7/2003 | Moutafis | A61B 17/3203 604/22 |
| 2003/0167053 A1 * | 9/2003 | Taufig | A61M 1/0084 604/542 |
| 2004/0030349 A1 | 2/2004 | Boukhny | |
| 2004/0092987 A1 * | 5/2004 | Pein | A61B 17/32037 606/167 |
| 2004/0220564 A1 * | 11/2004 | Ho | A61B 10/02 606/47 |
| 2004/0243157 A1 * | 12/2004 | Connor | A61B 17/32001 606/159 |
| 2005/0023005 A1 * | 2/2005 | Log | A62C 35/58 169/16 |
| 2005/0124985 A1 * | 6/2005 | Takayama | A61B 18/26 606/15 |
| 2005/0251105 A1 * | 11/2005 | Peyman | A61M 1/0084 604/521 |
| 2006/0111663 A1 * | 5/2006 | Pein | A61B 17/3203 604/19 |
| 2007/0276421 A1 * | 11/2007 | Pein | A61B 17/3203 606/167 |
| 2008/0103504 A1 * | 5/2008 | Schmitz | A61B 17/320016 606/79 |
| 2008/0243157 A1 * | 10/2008 | Klein | A61B 17/3203 606/167 |
| 2009/0043320 A1 * | 2/2009 | Seto | A61B 17/3203 606/159 |
| 2009/0254075 A1 * | 10/2009 | Paz | A61B 17/3203 606/28 |
| 2009/0312696 A1 * | 12/2009 | Copa | A61M 25/007 604/43 |
| 2010/0217151 A1 * | 8/2010 | Gostout | A61B 1/00094 600/565 |
| 2011/0152908 A1 * | 6/2011 | Morris | A61B 17/32037 606/159 |
| 2012/0232341 A1 * | 9/2012 | Seto | A61B 1/00087 600/104 |
| 2013/0072958 A1 * | 3/2013 | Ressemann | A61B 17/24 606/199 |
| 2013/0116683 A1 * | 5/2013 | Shadduck | A61B 18/04 606/41 |
| 2013/0172828 A1 * | 7/2013 | Kappel | A61B 17/00234 604/272 |
| 2013/0274788 A1 * | 10/2013 | Jennings | A61B 17/0231 606/191 |

* cited by examiner

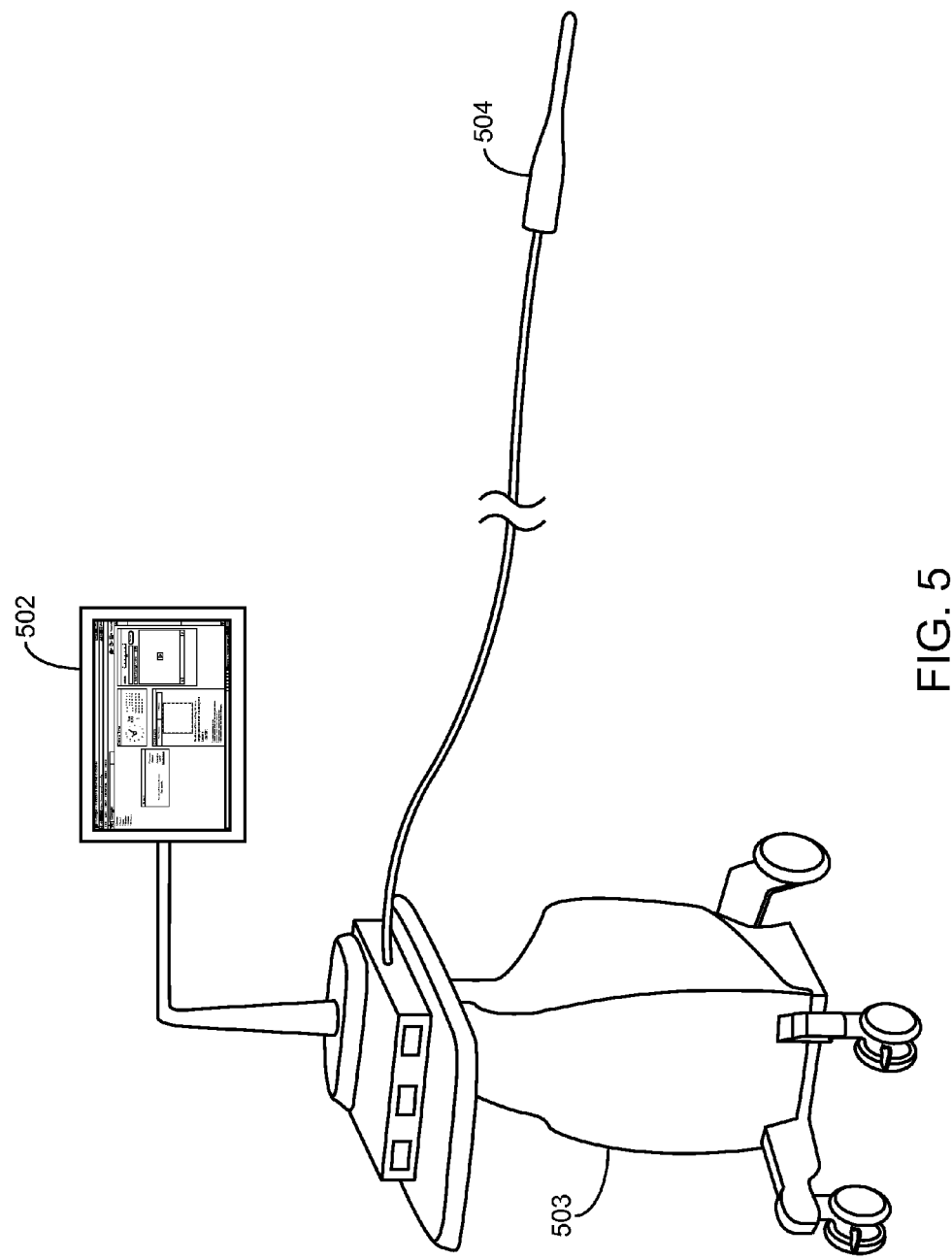

METHOD, APPARATUS, AND A SYSTEM FOR A WATER JET

CROSS-REFERENCE TO RELATED APPLICATIONS

Pursuant to 35 U.S.C. §119(e), this application claims priority to the filing date of U.S. Provisional Patent Application Ser. No. 61/793,108 filed on Mar. 15, 2013, the disclosure of which is herein incorporated by reference.

BACKGROUND OF THE INVENTION

Field of the Invention

The field of the present application pertains to medical devices. More particularly, the field of the invention pertains to an apparatus, system, and method for performing eye surgery with a waterjet.

Description of the Related Art

A cataract is a clouding of the lens in the eye that affects vision. Most cataracts are related to aging. Cataracts are very common in older people. By age 80, more than half of all Americans either have a cataract or have had cataract surgery.

The lens lies behind the iris and the pupil. It works much like a camera lens. It focuses light onto the retina at the back of the eye, where an image is recorded. The lens also adjusts the eye's focus, letting us see things clearly both up close and far away. The lens is made of mostly water and protein. The protein is arranged in a precise way that keeps the lens clear and lets light pass through it. But as we age, some of the protein may clump together and start to cloud a small area of the lens. This is a cataract. Over time, the cataract may grow larger and cloud more of the lens, making it harder to see.

Age-related cataracts can affect vision in two ways. First, clumps of protein reduce the sharpness of the image reaching the retina. The lens consists mostly of water and protein. When the protein clumps up, it clouds the lens and reduces the light that reaches the retina. The clouding may become severe enough to cause blurred vision. Most age-related cataracts develop from protein clumping. Second, the clear lens slowly changes to a yellowish/brownish color, adding a brownish tint to vision. As the clear lens slowly colors with age, it may gradually cause vision to have a brownish shade. At first, the amount of tinting may be small and may not cause a vision problem. Over time, increased tinting may make it more difficult to read and perform other routine activities.

Surgery is the only real treatment for cataracts. Each year, cataract surgeons in the United States perform over three million cataract surgeries. The vast majority of cataracts are removed using a procedure called extracapsular cataract extraction (ECCE). Extracapsular cataract extraction involves the removal of almost the entire natural lens while the elastic lens capsule (posterior capsule) is left intact to allow implantation of an intraocular lens. Less commonly this can be achieved by manual expression of the lens through a large (usually 10-12 mm) incision made in the cornea or sclera. Although it requires a larger incision and the use of stitches, this "large incision" method may be indicated for patients with very hard cataracts or other situations in which phacoemulsification is problematic.

Modern extracapsular cataract surgery is usually performed using a microsurgical technique called phacoemulsification, whereby the cataract is emulsified with an ultrasonic handpiece and then suctioned out of the eye. Before phacoemulsification can be performed, one or more incisions are made in the eye to allow the introduction of surgical instruments. The surgeon then removes the anterior face of the capsule that contains the lens inside the eye. A phacoemulsification probe is an ultrasonic handpiece with a titanium or steel needle. The tip of the needle vibrates at ultrasonic frequency to sculpt and emulsify the cataract while a pump aspirates particles through the tip. In some techniques, a second fine steel instrument called a chopper is used from a side port to help with mechanically chopping the nucleus into smaller pieces. The cataract is usually broken into numerous pieces and each piece is emulsified and aspirated out with suction. The nucleus emulsification makes it easier to aspirate the particles. After removing all hard central lens nucleus with phacoemulsification, the softer outer lens cortex is removed with suction only. As with other cataract extraction procedures, an intraocular lens implant (IOL), is placed into the remaining lens capsule.

One possible improvement to phacoemulsification is a cataract surgery performed with lasers. Femtosecond Laser cataract surgery is rapidly emerging as a potential technology that may allow for improved precision of incision formation and emulsification of the cataract.

Although phacoemulsification and laser-based cataract surgery work well for many patients, these technologies have several shortcomings. For example, phacoemulsification ultrasound probes must propagate ultrasound energy along the length of the probe, from a proximal transducer to a distal tip. This propagation may lead to transmission of ultrasound energy along the probe to tissues in and around the eye that do not benefit from the transmission. Current lens emulsifying probes generate cavitation energy that is initiated within the area of lens nucleus and radiates outwards towards the lens capsule. This places the lens capsule at risk for damage by this energy. Ultrasound probes also tend to generate more heat than would be desirable for a procedure in the eye. Finally, it may be quite difficult to steer an ultrasound probe around corners or bends, due to the mechanical requirements of propagating the ultrasound wave along the entire instrument. In other words, the probe may have to be rigid or at least more rigid than would be desirable.

Femtosecond laser systems have been devised to assist in the removal of cataracts. These devices are used to create the entry sites through the cornea and sclera into the eye, as well as to remove the anterior face of the capsule. In addition, the femotosecond laser energy can be focused within the lens nucleus itself, and used to "pre-chop" the lens nucleus into a number of pieces that can then be more easily removed with the phacoemulsification probe. However, these lasers can only fragment the center zone of the lens that is visible within the pupil (the iris blocks the peripheral lens from laser energy), so that fracture and removal of the peripheral lens by another method is still necessary and can actually increase surgical time. They are costly to own and operate and have the additional drawback of extending operative time.

Therefore, it would be advantageous to have a method and device for treating cataracts, and potentially other eye ailments, that included many of the advantages of phacoemulsification and laser procedures without at least some of the drawbacks Some existing solutions are discussed in several issued patents and publications. For example, U.S. Pat. No. 7,967,799 teaches a liquefaction hand-piece tip. However, the tip requires a standoff or spacer to keep the distal end from directly contacting delicate tissue. In another existing solution, United States publication 2004/0030349 creates pulses of fluid. However, the fluid needs to be heated.

Therefore, it would be beneficial to have a new method, apparatus, and system for performing surgery for various applications including eye, micro-surgery, and/or other emulsification applications.

SUMMARY OF THE INVENTION

Embodiments described herein are directed to a method, apparatus, and system for performing surgery for various applications including eye, micro-surgery, and/or other emulsification applications. Specifically, in one embodiment, a liquid jet apparatus may be used for manually performing eye surgery such as, cataract.

It would increase the safety of the procedure and reduce the risk of inadvertent lens capsule rupture to devise an energy delivery system whereby rather than the energy originating in the area of the center of the lens and radiating out towards the vulnerable capsule, the energy originates towards the periphery of the lens and is directed away from the lens capsule and towards the center of the nucleus. Ideally, such a method and device would be relatively simple to manufacture and implement, and would work well for performing cataract surgery without harming surrounding eye tissue. Also ideally, the method and/or device would be applicable to one or more other eye conditions.

In another embodiments, an apparatus with a laser source to deliver laser energy from a variety of configuration ports are discussed. In other embodiments, the liquid jet apparatus allows for multiple stages of fluid delivery.

In one embodiment, an apparatus for a horizontal chopper is discussed that supports centripetally delivered laser energy to facilitate cataract surgery. In another embodiment, an apparatus for a horizontal chopper is discussed that supports centripetally delivering a fluid to facilitate cataract surgery.

In one embodiment, an apparatus for a vertical chopper is discussed that facilitates cataract surgery by central core ablation. In another embodiment, an apparatus for a vertical chopper is discussed that facilitates impaling the central lens with low and directed energy.

In yet another embodiment, an apparatus with an integrated horizontal and vertical chopper is discussed.

In yet another embodiment, a system with a source analyzer, the previous embodiments of the apparatus, and a monitor to assist the eye surgeon in cataract surgery is discussed.

These and other aspects and embodiments will be described in greater detail below, in reference to the attached drawing figures.

BRIEF DESCRIPTION OF THE DRAWINGS

FIG. 5 is a perspective view of a system for cataract surgery, according to another embodiment of the present invention.

DETAILED DESCRIPTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The embodiments described herein are directed to method, apparatus, and system for performing eye surgery. In the case of a cataract in an eye, a liquid jet apparatus or system may be used to break apart a cataract into multiple, smaller pieces, which may then be suctioned from the eye using the probe or other suction means. This liquid could be a saline solution or other such fluid, and chemical or biological agents can be added in order to improve surgical outcomes, including agents that inhibit unwanted residual lens cell growth or inflammation after surgery. Although the method and device are typically described below in the context of treating cataracts, in various alternative embodiments, other eye conditions may be treated. The density of the crystalline lens is known to vary from one patient to another and so the pressure and profile of the fluid jet can be varied by the surgeon in order to control the cleaving activity of the fluid jet. It is envisioned that the fluid pressure would range from 100 PSI to 500 PSI and preferably between 150 to 400 PSI. Higher pressure should be available where necessary, and the surgeon should be able to command linear pressure control from zero up to the minimum necessary to achieve effective cleavage.

Figure 1:
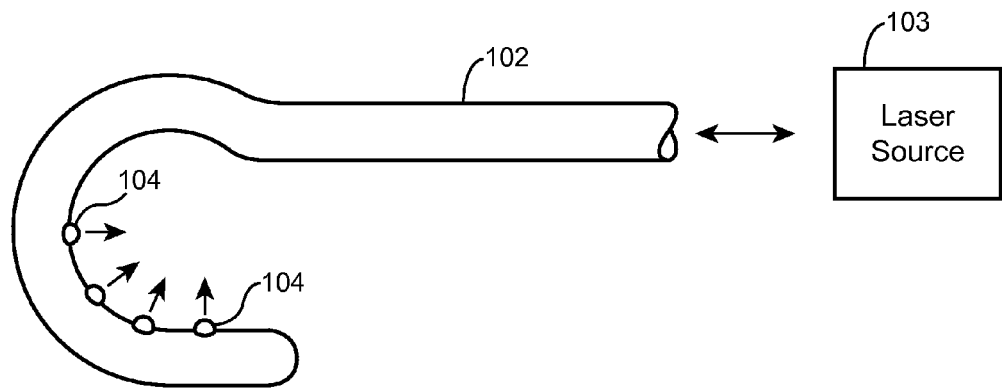
FIG. 1 is a perspective view of an apparatus with a horizontal chopper configuration, according to one embodiment of the present invention.
Figure 2:
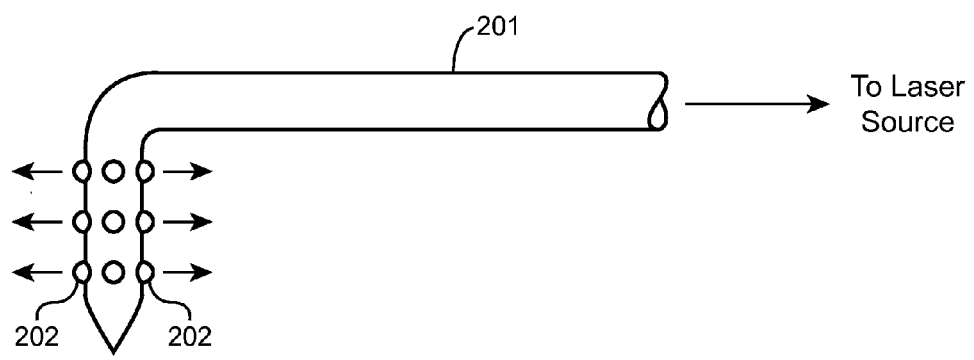
FIG. 2 is a perspective view of an apparatus with a vertical chopper configuration, according to one embodiment of the present invention.
Figure 4:
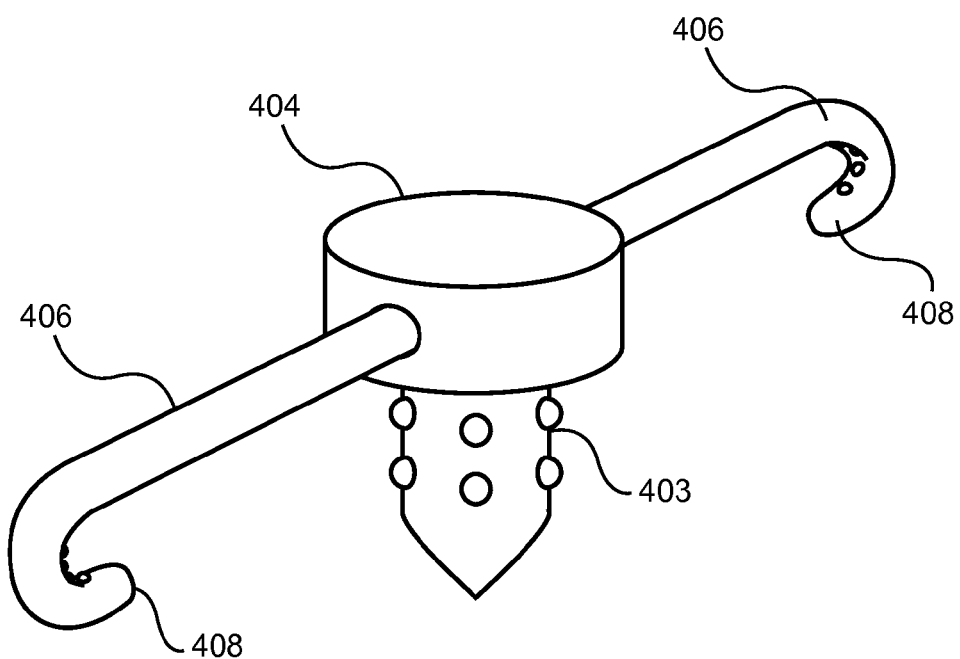
FIG. 4 is a perspective view of an apparatus of an integrated solution for a vertical and a horizontal chopper, according to another embodiment of the present invention.

In another embodiments, an apparatus with a laser source to deliver laser energy from a variety of configuration ports are discussed. In other embodiments, the liquid jet apparatus allows for multiple stages of fluid delivery. FIGS. 1, 2 and 4 depict various embodiments that may utilize laser or liquid jet energy from different configuration ports and different structural designs.

In one embodiment, an apparatus for a horizontal chopper is discussed that supports centripetally delivered laser energy to facilitate cataract surgery. In another embodiment, an apparatus for a horizontal chopper is discussed that supports centripetally delivering a fluid to facilitate cataract surgery. FIGS. 1 and 4 depict multiple embodiments of a horizontal chopper. One distinguishing aspect of this embodiment is the direction of energy from the periphery of the lens towards the center in order to reduce risk of damage to the lens capsule, as opposed to the current methods of lens fracture by phacoemulsification or laser wherein energy is directed outwards towards the capsule.

In one embodiment, an apparatus for a vertical chopper is discussed that facilitates cataract surgery by central core ablation. In another embodiment, an apparatus for a vertical chopper is discussed that facilitates impaling the central lens with low and directed energy. FIGS. 2 and 4 depict multiple embodiments of a vertical chopper.

In yet another embodiment, an apparatus with an integrated horizontal and vertical chopper is discussed. FIG. 4 depicts an embodiment of an apparatus that has integrated horizontal and vertical chopper functions.

In yet another embodiment, a system with a source analyzer, the previous embodiments of the apparatus, and a monitor to assist the eye surgeon in cataract surgery is discussed. FIGS. 5, 6A, 6B, and 6C depict a system design to facilitate cataract surgery.

FIG. 1 is a perspective view of an apparatus with a horizontal chopper configuration, according to one embodiment of the present invention. The source of energy 103 can be either laser or pressurized fluid. In this embodiment, the apparatus 102 has a candy cane configuration. In order to allow small incisional cataract surgery thereby minimizing surgically induced astigmatism, the nozzle tip and any delivery system will be below 2.75 mm. The tip of this probe is curved in order to allow the surgeon to reach around the equator of the lens within the lens cortex or epinucleus. The curved tip could be manufactured from metallic materials such as stainless steel or shape memory alloys such as Nitinol. It could also be a polymer such as polycarbonate. The leading edge of the tip can be constructed of a soft material such as silicone so as to minimize the risk of capsule rupture during placement. A curved tip made of a shape memory material such as Nitinol can be introduced via a straight cannula into the eye. Once the tip is advanced outside the cannula, the shaped nozzle will obtain its final curved shape. Various curves are possible in order to facilitate advancement of the tip around the equator of the lens nucleus. Various pull wire mechanisms known to the expert could be used to achieve the desired shape. It is also possible to change the shape of a Nitinol tip via heat activation.

In this embodiment, a plurality of ports 104 is dispersed on an inner semi-circular location of the apparatus. These ports can be designed so as to shape the profile of the fluid jet delivered. The ports can be designed so that multiple small columns (pencils) of high pressure fluid are delivered. They can also be designed so that slits or sheets of high pressure fluid are delivered to cut through the lens. In one embodiment, a laser source 103 supplies the laser energy to the apparatus 102. In this embodiment, the laser energy is delivered centripetally to the eye from the outputs of the plurality of ports 104. In another embodiment, a pressurizing fluid souce 103 supplies fluid to the apparatus 102. However, the claimed subject matter is not limited to the number of configuration ports 104 that are depicted. For example, one skilled in the art appreciates utilizing different number and different placement of the ports 104 to achieve the desired horizontal or substantially horizontal chopping function.

The instrument described in FIG. 1 can be placed as a single unit in the eye, or, in order to limit the penetration of energy beyond the center of the nucleus, two such tips can be placed in the eye 180 degrees apart and activated simultaneously.

In another embodiment, two stages of fluid delivery are utilized to facilitate cataract removal (FIG. 4, 408). In the first stage, a low pressure delivery of the fluid is utilized and directed toward the capsule between the nucleus and capsular plane. Subsequently, the second stage, a jet pressure is directed centripetally for lens fracture. As indicated in FIG. 4, 408, Two channels can be made available for the two stages of surgery, and while one channel is being employed for producing the lens cleaving jet pressure, the other can be used for fluid aspiration. This allows the maintenance of a steady volume within the anterior chamber, as well as removal of liquefied lens and cortical material. The aspiration flow rate should have a capacity of more than 1 cc per second.

FIG. 2 is a perspective view of an apparatus with a vertical chopper configuration, according to one embodiment of the present invention. In this embodiment, apparatus 201 utilizes a laser source to deliver laser energy to a plurality of ports 202 in a direction as indicated in the diagram. In one embodiment, the vertical chopper may be used to impale central lens with low and directed energy. Subsequently, in cataract surgery, the next step would be placement of the horizontal chopper to slice or chop the nucleus, then rotate and repeat the chopping process.

Figure 3:
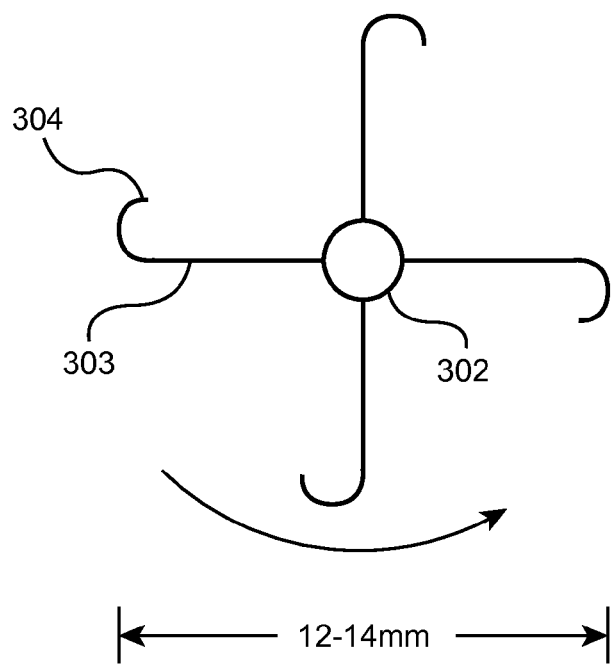
FIG. 3 is a perspective view of an apparatus with a turbine and flexible haptic arm configuration, designed to loosen equatorial lens cortex and epinuclear material in order to facilitate removal.

FIG. 3 is a perspective view of an apparatus with a turbine and a curved haptic arm configuration. The purpose of this device is to create friction within the residual epinucleus and cortex so as to facilitate cortical removal following fracture and removal of the lens nucleus. In this embodiment, the apparatus has a turbine 302 to provide rotation to the apparatus. In one embodiment, the rotation may be clockwise. In an alternative embodiment, the rotation may be counter clockwise.

The turbine 302 controls the rotating S shaped arms 303 with the hook shaped end 304.

In one embodiment, the hook shaped ends 304 may embody flexible haptics to minimize risk to the lens capsule and zonules, and to allow for feedback to the user. Also, in another embodiment, the entire arm and hook shaped end may utilize flexible haptics.

FIG. 4 is a perspective view of an apparatus of an integrated solution for a vertical and a horizontal chopper, according to another embodiment of the present invention.

In this embodiment, the integrated solution for the apparatus allows for a central centrifugal jet delivery probe 403 that is similar to the previously described embodiment in FIG. 2 with the horizontal probes depicted in connection with FIGS. 1 and 3 to allow for centripetal jet delivery and hydrodissection.

In this embodiment, the two arms that deliver centripetal energy away from the lens capsule and towards the center of the lens nucleus are placed 180 degrees apart so that when energy is simultaneously delivered, propagation of energy beyond the center from one probe is neutralized by the energy emitted from the probe located opposite, thus reducing the risk of damage to the lens capsule.

In this embodiment, the turbine 404 facilitates rotation of the arms 406 and hook ends 408 that may utilize two channels or have a valve for centripetal jet delivery for hydrodissection.

Also, in one embodiment, the centrifugal jet delivery probe 403 may utilize an ultrasound probe or an optical source analyzer to measure lens density. The ultrasound probe and optical source analyzer are depicted in connection with FIG. 5.

Also, in another embodiment, each hook shaped end could have a fiber optic probe coupled to the arm 303 to provide visualization.

In this embodiment, the apparatus facilitates centripetal and centrifugal forces to facilitate the eye surgery.

FIG. 5 is a perspective view of a system for cataract surgery, according to another embodiment of the present invention. In this embodiment, the system includes an ultrasound or optical source analyzer 503, with a tip 504 and a monitor 502 coupled to the system to display feedback and visualization to the eye surgeon.

In one embodiment, the tip 504 may utilize a close loop system that has a sensor to identify tissue and adjust pressure accordingly. In another embodiment, the tip pressure is adjusted based on measuring resistance and subsequently preceding with a different pressure based at least in part on the resistance measurement.

Figure 6A:
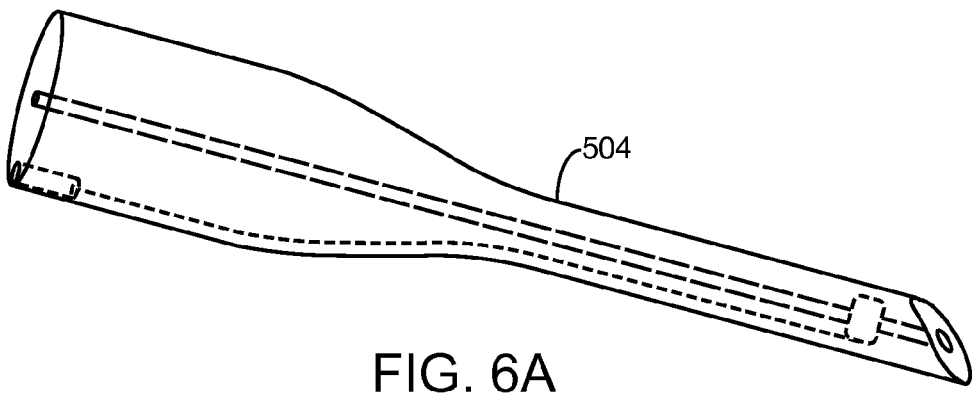
FIGS. 6A-6C depict a perspective view of a tip design for the system for cataract surgery, according to another embodiment of the present invention.
Figure 6B:
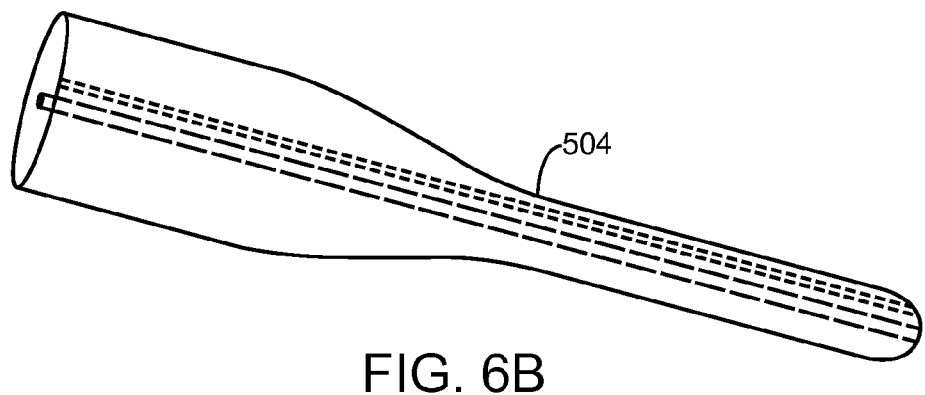
Figure 6C:
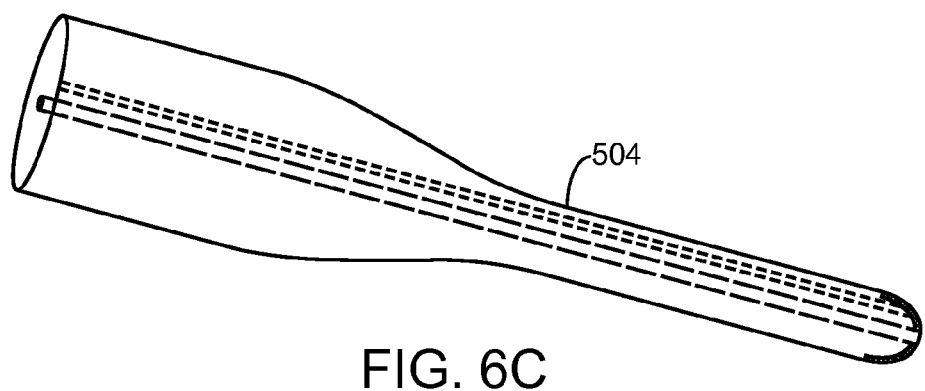

FIGS. 6A, 6B, and 6C depict a perspective view of a tip design for the system for cataract surgery, according to another embodiment of the present invention.

FIG. 6A details an embodiment of a tip 504 with an ultrasound sensor at a distal end with a center lumen for water or fluid injection.

FIG. 6B details an embodiment of a tip 504 that incorporates some of the features of the tip embodiment from FIG. 6A, and also includes an optical conduit.

FIG. 6C details an embodiment of a tip 504 that incorporates the features of the tip embodiment from FIG. 6A, and also includes a piezoelectrical sensor to detect hardness of the material.

Since a probe is being delivered around the lens nucleus, towards the posterior aspect of the lens, it allows the incorporation of a safety device to protect the lens capsule, including the posterior lens capsule. An expandable shell, balloon or membrane can be advanced along with the probe that is placed in front of the posterior capsule further protecting it from dispersed energy or potentially rupturing force. This protective element could be a polymer in the form of a balloon, or an expandable mechanical system such as a mesh. The protective element will be removed at the conclusion of nuclear fragmentation. This capsule protecting element can be made of materials commonly used in balloon angioplasty, or elastomeric materials or a combination. A mechanical expandable capsule protecting element can be made of shape memory materials such as Nitinol or stainless steel or other highly elastic alloys such as Elgiloy.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

The invention claimed is:

1. An apparatus comprising:
a horizontal chopper to perform an eye surgery, wherein the horizontal chopper comprises a proximal end connectable to an energy source and a distal end insertable into a human eye,
wherein the distal end comprises a hook-shaped tip comprising a semi-circular region, the semi-circular region comprising:
a first portion comprising a plurality of ports positioned to direct energy in a centripetal manner from a periphery of a lens in the eye toward a center of the lens and towards the center of the semi-circular region of the hook-shaped tip; and
a second portion that is devoid of the plurality of ports, wherein the second portion is connected to the energy source and wherein the first portion is connected to the energy source only via the second portion, wherein the energy enters into the semi-circular region at a first end of the second portion, travels from the second portion to the first portion via a second end of the second portion and exits from the plurality of ports in the first portion.

2. The apparatus of claim 1 wherein the horizontal chopper includes a centripetal jet delivery to perform hydrodissection, and wherein the plurality of ports deliver centripetal energy away from a capsule of the lens.

3. The apparatus of claim 1 wherein the energy source is a fluid system.

4. The apparatus of claim 1 wherein the energy source is a laser system.

5. The apparatus of claim 1 wherein the apparatus further comprises a vertical chopper integrated with the horizontal chopper.

6. The apparatus of claim 5 wherein the vertical chopper configured to impale the central lens with a low and directed energy.

7. The apparatus of claim 1 wherein the horizontal chopper comprises a first and a second arm placed substantially 180 degrees apart, to neutralize propagation past the center of the lens to reduce risk of damage to a capsule of the lens.

8. The apparatus of claim 1 wherein the plurality of ports is configured to direct columns of high pressure fluid in a centripetal manner from a periphery of the lens in the eye toward the center of the lens.

9. The apparatus of claim 8, wherein the pressure of the fluid ranges from 100 PS to 500 PSI.

10. The apparatus of claim 8, wherein the pressure of the fluid ranges from 150 PS to 400 PSI.

11. The apparatus of claim 8, wherein the fluid comprises saline.

12. The apparatus of claim 1 wherein the plurality of ports is configured to direct laser energy in a centripetal manner from a periphery of the lens in the eye toward the center of the lens.

* * * * *